(12) United States Patent
Isobe et al.

(10) Patent No.: US 8,371,171 B2
(45) Date of Patent: Feb. 12, 2013

(54) ULTRASONIC INSPECTION APPARATUS

(75) Inventors: Hideo Isobe, Tokyo (JP); Takahiro Ikeda, Kanagawa-ken (JP); Noriyuki Yamane, Tokyo (JP); Ryoichi Arai, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 242 days.

(21) Appl. No.: 12/918,907

(22) PCT Filed: Feb. 26, 2009

(86) PCT No.: PCT/JP2009/053601
§ 371 (c)(1),
(2), (4) Date: Aug. 23, 2010

(87) PCT Pub. No.: WO2009/107746
PCT Pub. Date: Sep. 3, 2009

(65) Prior Publication Data
US 2011/0000300 A1  Jan. 6, 2011

(30) Foreign Application Priority Data

Feb. 26, 2008  (JP) .................................. 2008-044308

(51) Int. Cl.
*G01N 29/265* (2006.01)
*G01N 29/06* (2006.01)
(52) U.S. Cl. ............................... 73/602; 73/634; 73/640
(58) Field of Classification Search .................. 73/602, 73/633, 634, 640
See application file for complete search history.

(56) References Cited

U.S. PATENT DOCUMENTS 3,678,736 A  7/1972 May
3,898,838 A  8/1975 Connelly
3,978,714 A  9/1976 Shraiber et al.
(Continued)

FOREIGN PATENT DOCUMENTS

JP  58-166195 U  11/1983
JP  63-309852 A  12/1988
(Continued)

OTHER PUBLICATIONS

Translation of International Preliminary Report on Patentability of PCT/JP2009/053601, dated Oct. 5, 2010, 6 pages.
(Continued)

*Primary Examiner* — Peter MacChiarolo
*Assistant Examiner* — Rose M Miller
(74) *Attorney, Agent, or Firm* — Foley & Lardner LLP

(57) ABSTRACT

There is provided an ultrasonic inspection apparatus using scanning path information with high accuracy at a time of ultrasonic flaw inspection. The ultrasonic inspection apparatus includes: a measurement unit measuring a distance to a surface of the object to be inspected to obtain measurement data including a group of points; a shape data generation unit, by using the measurement data including the group of points obtained by the measurement unit, for generating shape data of the surface of the object to be inspected including the group of points having position information represented by a coordinate system of the scanner mechanism; and a path information generation unit, by using the shape data generated by the shape data generation unit, for calculating a passage point on the surface of the object to be inspected that forms a scanning path of the ultrasonic transducer, and generating the scanning path information of the ultrasonic transducer in which a normal vector of the passage point on the surface of the object to be inspected and an opening surface of the ultrasonic transducer intersect each other, and a distance between the passage point and a center of the opening surface of the ultrasonic transducer is constant.

5 Claims, 8 Drawing Sheets

U.S. PATENT DOCUMENTS

| | | | |
|---|---|---|---|
| 4,881,177 A * | 11/1989 | McClean et al. | 700/258 |
| 5,214,616 A | 5/1993 | Terhune et al. | |
| 5,335,547 A | 8/1994 | Nakajima et al. | |
| 6,378,376 B1 | 4/2002 | Derman et al. | |
| 7,181,970 B2 * | 2/2007 | Haase et al. | 73/621 |
| 7,448,271 B2 | 11/2008 | Duncan et al. | |
| 7,496,456 B2 | 2/2009 | Hiyama et al. | |
| 7,891,248 B2 | 2/2011 | Hough et al. | |
| 7,921,575 B2 * | 4/2011 | Little et al. | 33/503 |
| 8,100,015 B2 | 1/2012 | Karasawa et al. | |
| 8,179,132 B2 * | 5/2012 | Wu et al. | 324/238 |
| 2007/0039390 A1 | 2/2007 | Duncan et al. | |
| 2009/0288490 A1 * | 11/2009 | Maruyama et al. | 73/633 |

FOREIGN PATENT DOCUMENTS

| | | |
|---|---|---|
| JP | 03-077057 A | 4/1991 |
| JP | 05-045347 A | 2/1993 |
| JP | 2553867 B | 8/1996 |
| JP | 2720077 B2 | 11/1997 |
| JP | 2005-106654 A | 4/2005 |
| JP | 2005-300363 A | 10/2005 |
| JP | 3766210 B2 | 2/2006 |
| JP | 2006-317417 A | 11/2006 |
| JP | 2007-192649 A | 8/2007 |
| WO | WO 2007/021541 A2 | 2/2007 |

OTHER PUBLICATIONS

Translation of International Preliminary Report on Patentability of PCT/JP2009/053600, dated Oct. 5, 2010, 7 pages.

U.S. Appl. No. 12/918,904, filed Aug. 23, 2010, Isobe.

H. Isobe, U.S. PTO Office Action, U.S. Appl. No. 12/918,904, dated Jun. 20, 2012, 16 pages.

* cited by examiner

ULTRASONIC INSPECTION APPARATUS

TECHNICAL FIELD

The present invention relates to an ultrasonic inspection apparatus, and more particularly to an ultrasonic inspection apparatus that performs scanning with high accuracy in an ultrasonic flaw inspection.

BACKGROUND ART

To inspect a defect in a structure or a component, or a peeling state of a void or a joint, an ultrasonic inspection apparatus is used that can visualize such a state. The ultrasonic inspection apparatus uses an ultrasonic transducer constituted by a piezoelectric conversion unit formed into a matrix or linear array shape to scan an object to be inspected and inspect a defect or the like.

The ultrasonic inspection apparatus includes a scanner mechanism that drives the ultrasonic transducer. The scanner mechanism is constituted by a Cartesian robot having an X-axis, a Y-axis, a Z-axis, and a required axis such as an A-axis (rotation axis in an X-axis direction), a B-axis (rotation axis in a Y-axis direction), or a C-axis (rotation axis in a Z-axis direction), or an industrial robot basically including an arm mechanism. The scanner mechanism is driven based on control by a control mechanism or the like, and thus the ultrasonic transducer mounted to the scanner mechanism automatically performs a flaw inspection of a predetermined range on a surface of the object to be inspected.

For the ultrasonic transducer to automatically perform a flaw inspection of a predetermined range, scanning path information of the scanner mechanism needs to be previously generated. The scanning path information is generated based on a surface shape of the object to be inspected, for example, with an opening width of the ultrasonic transducer as one scanning width.

A method of generating scanning path information includes a method of previously generating scanning path information using computer software based on shape design data of an object to be inspected. By this method, scanning path information can be relatively easily prepared. However, the prepared scanning path information is scanning path information based on ideal shape design data, and there is a possibility that a shape of an actual object to be inspected does not match a shape of the object to be inspected on the shape design data due to working accuracy in production of the object to be inspected. Furthermore, in an ultrasonic flaw inspection, the object to be inspected is placed in a predetermined position in the scanner mechanism, but it is difficult to place an object to be inspected having a complicated shape in a predetermined position with high reproducibility.

Another method of generating scanning path information includes a method of driving an ultrasonic transducer with a scanner mechanism on a surface of an object to be inspected, thus teaching and registering each of passage points on an actual scanning path, and generating, as scanning path information, the passage points of the scanner mechanism connected as a scanning path. In this method, the scanner mechanism is driven at each of the passage points on the scanning path to teach and register the scanning path of the scanner mechanism, which requires an enormous amount of time and operation. In particular, if a driving unit provided in the scanner mechanism has a complicated configuration, a very complicated procedure and operation are required.

To perform an ultrasonic flaw inspection with high accuracy, ultrasound transmitted by an ultrasonic transducer needs to be incident on an inspection region of an object to be inspected at a constant angle. For an ultrasonic inspection apparatus that performs a flaw inspection by an aperture synthesis, a constant distance needs to be maintained between an ultrasonic transducer and a surface of an object to be inspected.

Then, an ultrasonic flaw inspection apparatus has been proposed that can hold an object to be inspected and an ultrasonic transducer with a constant distance therebetween, and can cause ultrasound to be incident on the object to be inspected at a constant angle (for example, refer to Japanese Patent Laid-Open Publication No. 63-309852 (Patent Document 1)).

The ultrasonic flaw inspection apparatus disclosed in the above Publication includes a distance sensor at a lower end of a drive shaft substantially perpendicular to a scanning stage of a scanner mechanism, and the distance sensor performs scanning on the object to be inspected. Based on measurement data of the distance between the object to be inspected and the distance sensor obtained by scanning, shape data of the object to be inspected that is coordinate data of the scanner mechanism is calculated and stored in a memory. Further, in scanning, scanning path information with each point of the shape data of the object to be inspected as a passage point is prepared and open loop control of a driving mechanism is performed.

Furthermore, an automatic ultrasonic flaw inspection method has been also proposed of obtaining shape data of an object to be inspected by performing an interpolation using a spline function, and performing position control of an ultrasonic transducer (for example, see Japanese Patent Laid-Open Publication No. 5-45347 (Patent Document 2)).

The automatic ultrasonic flaw inspection method performs an interpolation of obtained distance data using a spline function, thereby reducing time and labor required for preparing shape data.

With the ultrasonic flaw inspection apparatus in Patent Document 1, to obtain the shape data of the object to be inspected, shape data including a passage point on a scanning path on the object to be inspected needs to be previously obtained, which involves an enormous time. In addition, when it is required to change the scanning path after generation of the scanning path information, it was necessary to again obtain the shape data.

Moreover, the automatic ultrasonic flaw inspection method disclosed in Patent Document 2 can prepare shape data with distance data at a small number of points by performing the interpolation using the spline function. However, in order to generate the scanning path information with higher accuracy, it is essential to obtain distance data at a larger number of points so as to eliminate a need for an interpolation as much as possible.

DISCLOSURE OF THE INVENTION

The present invention is achieved in view of such circumstances, and an object thereof is to provide an ultrasonic inspection apparatus that generates scanning path information with high accuracy and efficiency based on shape data including a group of multiple points on a surface of an object to be inspected to thereby make it possible to perform an ultrasonic flaw inspection with high accuracy.

To achieve the above-described object, the present invention provides an ultrasonic inspection apparatus, which includes: an ultrasonic transducer including a plurality of piezoelectric transducers; a flaw inspection device including a driving element selection unit connected to the plurality of piezoelectric transducers and adapted to select a required piezoelectric transducer in response to a drive signal from a signal generation unit, a signal detection circuit that causes ultrasound emitted from the piezoelectric transducer selected by the driving element selection unit to be incident on an object to be inspected, receives a reflection echo of the ultrasound, and detects an electric signal of the reflection echo, and a signal processing unit that calculates the detected electric signal of the reflection echo to thereby generate image information of an inside of the object to be inspected; a scanner mechanism including a driving section that moves the ultrasonic transducer in three axial directions intersecting each other on the object to be inspected, and a rotating section that rotates the ultrasonic transducer around a rotation axis in at least one axial direction among the three axial directions; a measurement unit measuring a distance to a surface of the object to be inspected to obtain measurement data including a group of points; a shape data generation unit, by using the measurement data including the group of points obtained by the measurement unit, for generating shape data of the surface of the object to be inspected including the group of points having position information represented by a coordinate system of the scanner mechanism; and a path information generation unit, by using the shape data generated by the shape data generation unit, for calculating a passage point on the surface of the object to be inspected that forms a scanning path of the ultrasonic transducer, and generating the scanning path information of the ultrasonic transducer in which a normal vector of the passage point on the surface of the object to be inspected and an opening surface of the ultrasonic transducer intersect each other, and a distance between the passage point and a center of the opening surface of the ultrasonic transducer is constant.

The ultrasonic inspection apparatus according to the present invention generates the shape data of the surface of the object to be inspected, and generates the scanning path information with high accuracy and efficiency based on the shape data, thereby performing an ultrasonic flaw inspection with high accuracy.

BEST MODE FOR CARRYING OUT THE INVENTION

Embodiments of an ultrasonic inspection apparatus according to the present invention will be described hereunder with reference to the accompanying drawings.

Figure 1:
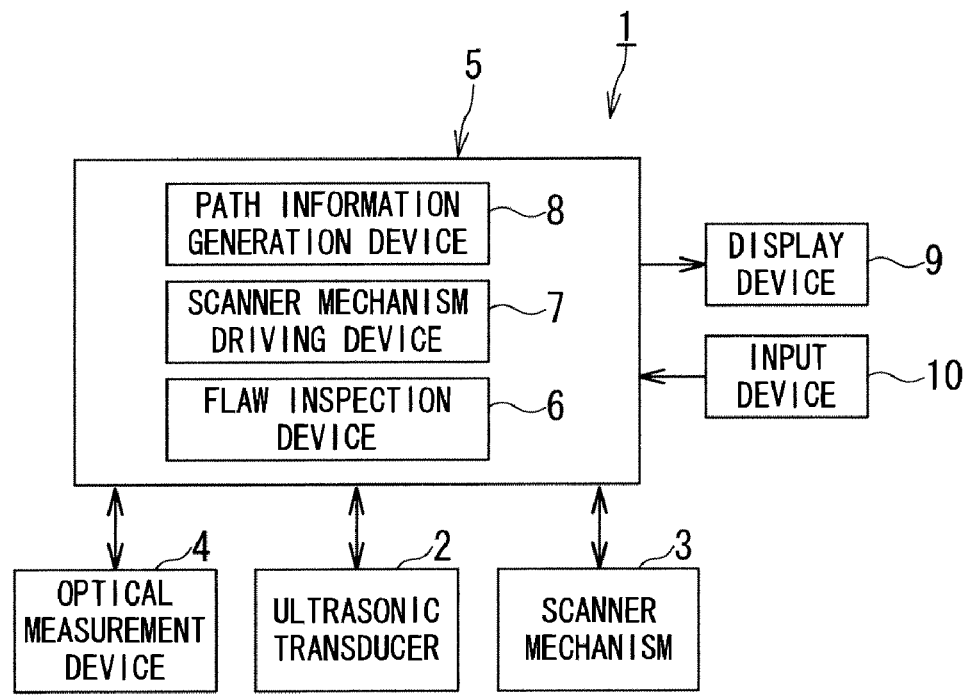
FIG. 1 is a schematic general configuration diagram showing an ultrasonic inspection apparatus according to the present invention.

FIG. 1 is a schematic general configuration diagram as an example of an ultrasonic inspection apparatus 1 according to the embodiment.

In the ultrasonic inspection apparatus 1, an ultrasonic transducer 2 constituted by a piezoelectric conversion unit 23 formed into a matrix or linear array shape scans a surface of an object to be inspected by using a scanner mechanism 3. Thus, an internal defect, a void and peeling in the object to be inspected can be visualized by using an aperture synthesis method.

The ultrasonic inspection apparatus 1 includes an ultrasonic transducer 2, a scanner mechanism 3, an optical measurement device 4, and an apparatus body 5 which includes a flaw inspection device 6, a scanner mechanism driving device 7 and a path information generation device 8.

The apparatus body 5 also includes a display device 9 that displays a two- or three-dimensional flaw inspection image or the like obtained by an ultrasonic flaw inspection, and an input device 10 that receives inputs of various instructions.

Figure 2:
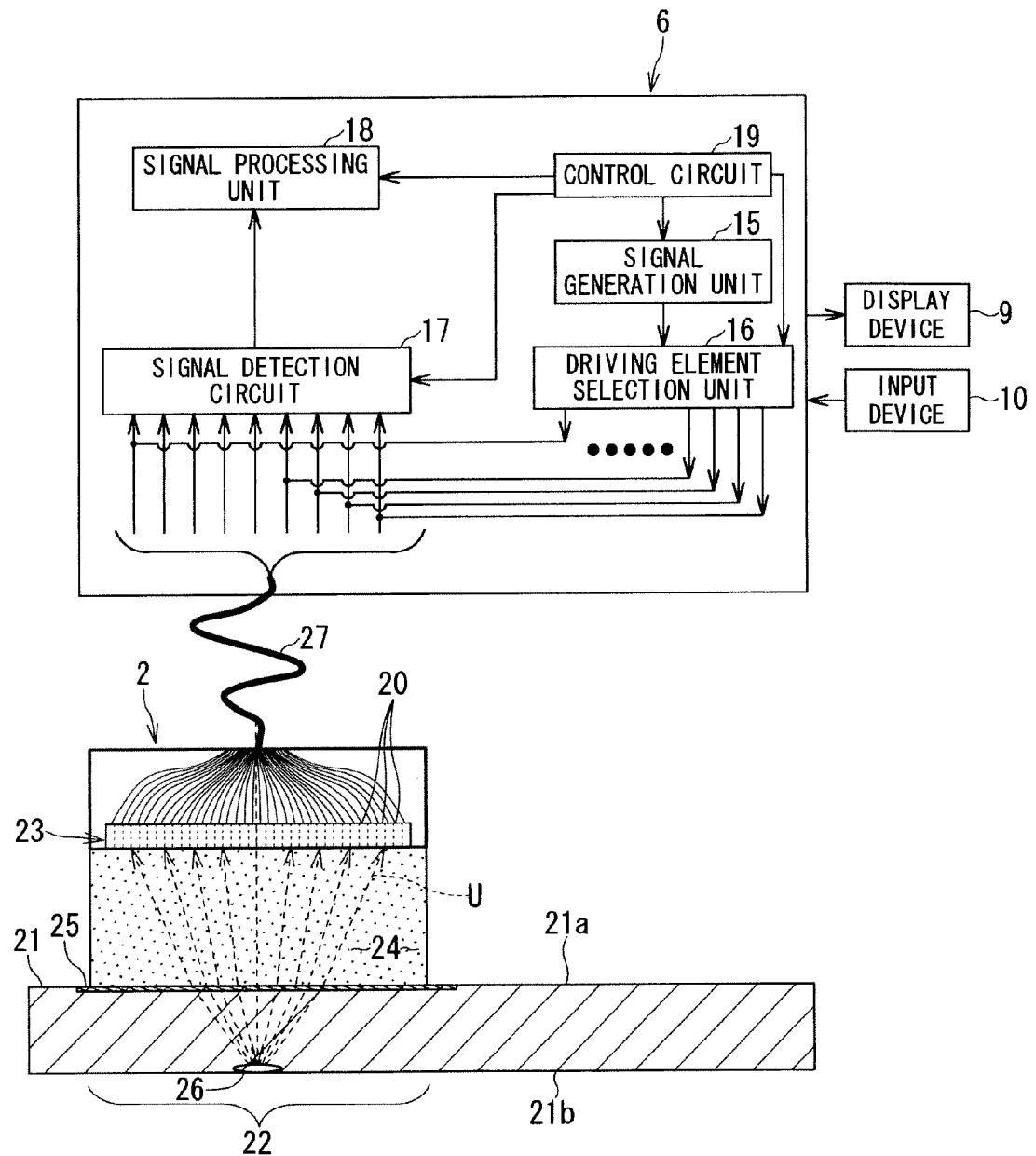
FIG. 2 is a functional configuration diagram illustrating the ultrasonic transducer and a flaw inspection device provided for an apparatus body.

FIG. 2 is a functional diagram illustrating structures of the ultrasonic transducer 2 and the flaw inspection device 6 provided in the apparatus body 5.

The flaw inspection device 6 includes a signal generation unit 15 that generates a drive signal, a driving element selection unit 16, a signal detection circuit 17, a signal processing unit 18 and a control circuit 19.

The signal generation unit 15 generates a drive signal for driving the ultrasonic transducer 2.

The driving element selection unit 16 selects the drive signal from the signal generation unit 15 and selectively drives piezoelectric transducers or oscillators (piezoelectric conversion elements) 20 in the ultrasonic transducer 2.

The signal detection circuit 17 serves to detect a reflection echo of ultrasound, via the ultrasonic transducer 2, as an electric signal, emitted from the ultrasonic transducer 2, applied to the inspection region 22 (target region) of the object to be inspected 21, and reflected in the inspection region 22.

The signal processing unit 18 performs a series of processes such as amplification, A/D conversion, and visualization of the electric signal of the reflection echo detected by the signal detection circuit 17, and then, generates ultrasound image information.

The display device 9 includes a display unit, a calculation unit, a storage unit, and the like. As the display unit, a flat panel display such as a liquid crystal display, an LED (light emitting diode), an EL (electro luminescence), a VFD (vacuum fluorescent display), or a PDP (plasma display panel) may be used. The display device 9 generates and displays a two- or three-dimensional flaw inspection image as required on the basis of the ultrasound image information processed by the signal processing unit 18. The input device 10 is constituted by a keyboard or a mouse.

The control circuit 19 controls operations of the signal generation unit 15, the driving element selection unit 16, the signal detection circuit 17, the signal processing unit 18, and the display device 9. That is, the control circuit 19 controls a series of operations such as transmission and reception of the ultrasound, the imaging and the display.

When the control circuit 19 receives an instruction input to start an inspection from the input device 10, the control circuit 19 first instructs the signal generation unit 15 to generate a drive signal of the ultrasonic transducer 2 to generate ultrasound image information of the inspection region 22 of the object to be inspected 21. Furthermore, in order to select a piezoelectric transducer 20 to which a drive signal is supplied among the plurality of piezoelectric transducers 20 constituting the ultrasonic transducer 2, the control circuit 19 instructs the driving element selection unit 16 to select the piezoelectric transducer 20 to which the drive signal is supplied.

When the piezoelectric transducer 20 is driven, the ultrasound is emitted to the inspection region 22 of the object to be inspected 21. A reflection echo based on the ultrasound is received by the piezoelectric transducer 20 and converted into an electric signal. The reflection echo is received simultaneously by the plurality of piezoelectric transducers 20. At this time, the control circuit 19 instructs the signal detection circuit 17 to select the piezoelectric transducer 20 so as to select a reflection echo required for generating the ultrasound image information.

The control circuit 19 instructs the signal processing unit 18 to perform a series of processes such as amplification, A/D conversion and visualization of the electric signal of the reflection echo to thereby obtain the ultrasound image information (for visualization). Then, the control circuit 19 sends a control instruction to display the visualized information on the display device 9.

The input device 10 inputs an instruction to start or finish an inspection or switch an image, or inputs the setting of an inspection condition into the control circuit 19 and performs an operation of the ultrasonic inspection apparatus 1.

Next, the ultrasonic transducer 2 will be described.

The ultrasonic transducer 2 includes a piezoelectric conversion unit 23 in which the multiple piezoelectric transducers (oscillators) 20 as the piezoelectric conversion elements are arranged in an m×n matrix. The piezoelectric conversion unit 23 constitutes an ultrasonic sensor that is a matrix sensor. In the piezoelectric conversion unit 23, the piezoelectric transducers 20 may be arranged in a line or a cross line (array) instead of the matrix shape to form an array sensor.

The drive signal generated by the signal generation unit 15 is selected by the driving element selection unit 16 and added to each of the piezoelectric transducers 20 in the ultrasonic transducer 2. A driving order of each or several of the piezoelectric transducers 20 is determined by the selection by the driving element selection unit 16, and each piezoelectric transducer 20 is driven at required driving timing so as to transmit the ultrasound.

The ultrasound emitted by each piezoelectric transducer 20 is applied to the inspection region 22 of the object to be inspected 21, and a part of the ultrasound is reflected from a density boundary layer of the inspection region 22 to form the reflection echo. The reflection echo is received by the ultrasonic transducer 2 (matrix sensor) that is an ultrasound sensor.

A shoe member 24 that is a liquid or solid acoustic propagation medium is bonded to a side of an emitting and receiving surface constituting an ultrasonic sensor surface of the ultrasonic transducer 2, specifically, a side of the object to be inspected 2. A couplant 25 for acoustic matching of ultrasound is provided between the shoe member 24 and the object to be inspected 21. The couplant 25 is formed of a low-volatile gel-like liquid. In a case where the shoe member 24 that is an acoustic propagation medium is composed of a liquid such as water, the couplant 25 will not be required.

The ultrasound successively emitted from the piezoelectric transducers 20 in the ultrasonic transducer 2 passes through the shoe member 24 as the acoustic propagation medium and the couplant 25 and is then incident on the inspection region 22 of the object to be inspected 21. The ultrasound is then reflected by boundary layers of the inspection region 22.

The reflection echo U of the ultrasound reflected by the boundary layers, such as the surface 21a of the object to be inspected 21, a boundary surface, a bottom surface 21b, or an internal defect 26, passes from the object to be inspected 21 through the shoe member 24 and is received by the piezoelectric transducers 20 of the ultrasonic transducer 2 with time differences. The reflection echo U oscillates the piezoelectric transducers 20 and is converted into an electric signal (electric echo signal). The electric echo signal is then input to the signal detection circuit 17 via a signal cable 27 and detected for each piezoelectric transducer 20.

The signal detection circuit 17 is connected, in an aligned state, to each piezoelectric transducer 20 in the ultrasonic transducer (ultrasonic sensor) 2 via the signal cable 27. The electric echo signal generated by each piezoelectric transducer 20 of the piezoelectric conversion unit 23 is guided to the signal detection circuit 17 via the signal cable 27. A drive signal from the signal generation unit 15 is guided to each piezoelectric transducer 20 of the piezoelectric conversion unit 23 via the driving element selection unit 16 using the signal cable 27.

An operation of the flaw inspection device of the ultrasonic inspection apparatus 1 will be described hereunder.

When the drive signal is applied to a piezoelectric transducer 20 in the m-th row and n-th column among the piezoelectric transducers 20 in the ultrasonic transducer 2, the piezoelectric transducer 20 is operated to generate ultrasound as a piezoelectric member to emit the ultrasound. The emitted ultrasound passes through the shoe member 24 and the couplant 25 and is applied to the inspection region 22 of the object to be inspected 21.

The ultrasound applied to the inspection region 22 of the object to be inspected 21 is partially reflected by the density boundary layer of the inspection region 22 to be the reflection echo. The reflection echo U passes through the couplant 25 and the shoe member 24 and is returned to the ultrasonic transducer 2, and received by the piezoelectric transducers 20 with time differences. The reflection echo U is converted into an electric signal (an electric echo signal) by a piezoelectric conversion by the piezoelectric transducers 20, and the signal is transmitted via the signal cable 27 and detected by the signal detection circuit 17.

A plurality of electric echo signals required for an inspection among electric echo signals detected by the signal detection circuit 17 are guided to the signal processing unit 18. The signal processing unit 18 performs a series of processes such as amplification, A/D conversion and visualization of the guided electric echo signals, and generates ultrasound image information. The generated ultrasound image information is guided to the display device 9 and imaged, and then is displayed as a two- or three-dimensional flaw inspection image.

Figure 3:
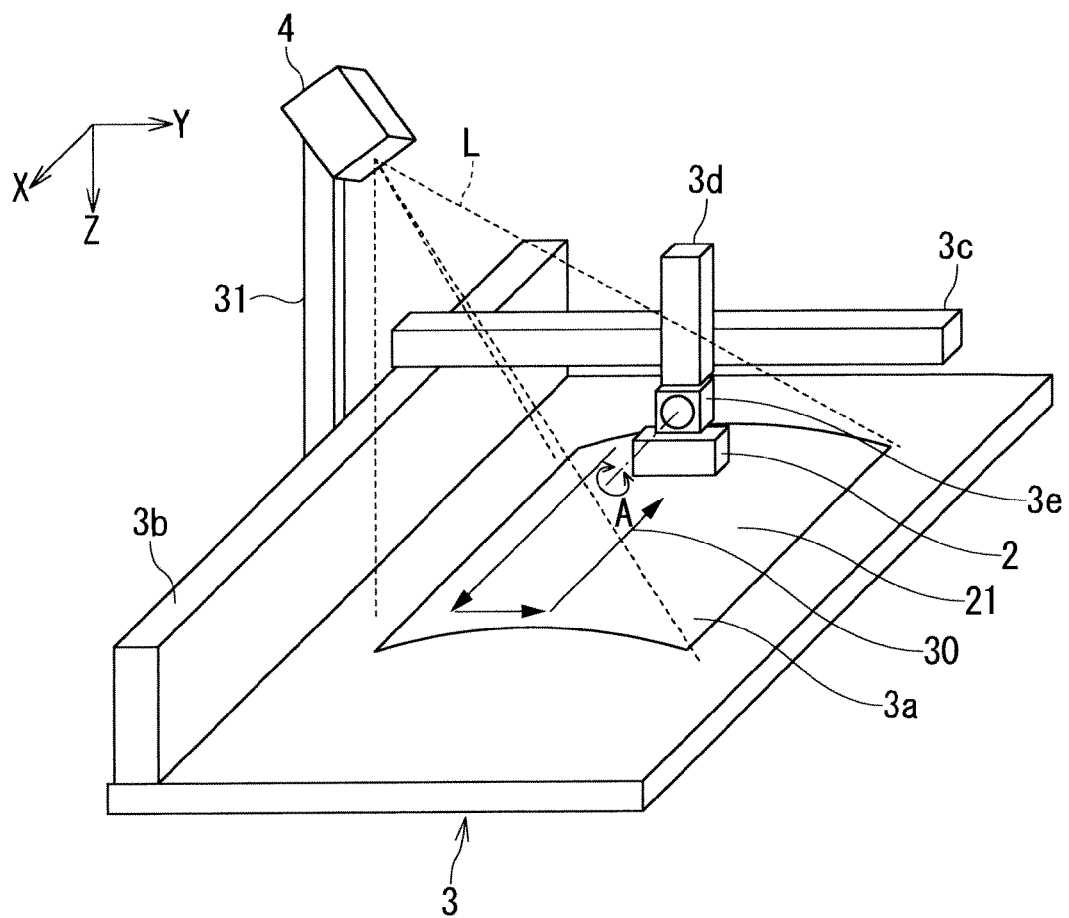
FIG. 3 is a configuration diagram illustrating a scanner mechanism and an optical measurement device.

FIG. 3 is a diagram illustrating structures of the scanner mechanism 3 and the optical measurement device 4.

The scanner mechanism 3 includes a scanning stage 3a on which the object to be inspected 21 is placed, a securing portion 3b substantially vertically secured to one side of the scanning stage 3a, an X-axis driving portion 3c driven on the securing portion 3b in an X-axis direction, and a YZ-axis driving portion 3d driven in Y-axis and Z-axis directions. At a lower end of the YZ-axis driving portion 3d, an A-axis rotating portion 3e that rotates around an A-axis, which is a rotation axis in the X-axis direction, and the ultrasonic transducer 2 are sequentially formed. The X-axis, the Y-axis and the Z-axis intersect each other.

The X-axis driving portion 3c, the YZ-axis driving portion 3d and the A-axis rotating portion 3e of the scanner mechanism 3 are driven in the X-axis, Y-axis and Z-axis directions and around the A-axis on the scanning stage 3a based on control signals transmitted from the scanner mechanism driving device 7 in the apparatus body 5. The control signals transmitted from the scanner mechanism driving device 7 to the scanner mechanism 3 are generated based on scanning path information obtained from the path information generation device 8 of the apparatus body 5 or information input from the input device 10.

The object to be inspected 21 is placed on the scanning stage 3a of the scanner mechanism 3. The ultrasonic transducer 2 scans the object to be inspected 21 placed on the scanning stage 3a in accordance with the driving of the X-axis driving portion 3c, the YZ-axis driving portion 3d and the A-axis rotating portion 3e. The scanner mechanism 3 may be configured so that the securing portion 3b is directly secured to the object to be inspected 21 for scanning without providing the scanning stage 3a.

For the ultrasonic transducer 2 to scan the surface of the object to be inspected 21, it is necessary to previously prepare scanning path information.

Scanning path information 30 is information on a path along which the ultrasonic transducer 2 secured to the lower end of the YZ-axis driving portion 3d of the scanner mechanism moves to scan the object to be inspected 21. The scanning path information 30 in FIG. 3 is shown by arrows in the X-axis and Y-axis directions on the object to be inspected 21. The scanner mechanism driving device 7 drives the X-axis driving portion 3c, the YZ-axis driving portion 3d and the A-axis rotating portion 3e based on the scanning path information 30, and thus, the ultrasonic transducer 2 automatically scans the object to be inspected 21.

Generally, conventional scanning path information is generated by a method of preparing information using computer software based on shape design data of an object to be inspected, or a method of actually driving a scanner mechanism 3 to teach and register each passage point on a scanning path. Further, it is necessary for the scanning path information to be prepared so that ultrasound can be perpendicularly incident on the surface of the object to be inspected 21 and a distance between a center of the opening surface of the ultrasonic transducer 2 and the surface of the object to be inspected 21 is constant. However, it is difficult to generate the scanning path information with high accuracy even in the use of either one of the above-described methods.

In the ultrasonic inspection apparatus 1 of the present invention, with the object to be inspected 21 being placed on the scanner mechanism 3, the optical measurement device 4 measures a shape of the surface of the object to be inspected 21, and calculates a group of points of shape data at minute intervals, thereby preparing scanning path information with high accuracy. Because of this reason, the scanner mechanism 3 is controlled based on the scanning path information, and thus, the ultrasound emitted from the ultrasonic transducer 2 can be perpendicularly incident on the surface of the object to be inspected 21, that is a cylindrical surface as shown in FIG. 3, and the scanning operation can be performed so that the distance between the center of the opening surface of the ultrasonic transducer 2 and the surface of the object to be inspected 21 becomes constant.

The optical measurement device 4 is placed on a shaft 31 provided in the Z-axis direction on the securing portion 3b of the scanner mechanism 3 so as to be able to apply a laser light L onto the scanning stage 3a constituting a two-dimensional surface of the scanner mechanism 3. The optical measurement device 4 is constituted by for example, a device, such as a three-dimensional laser scanner, capable of scanning a certain area at high speed.

Figure 4:
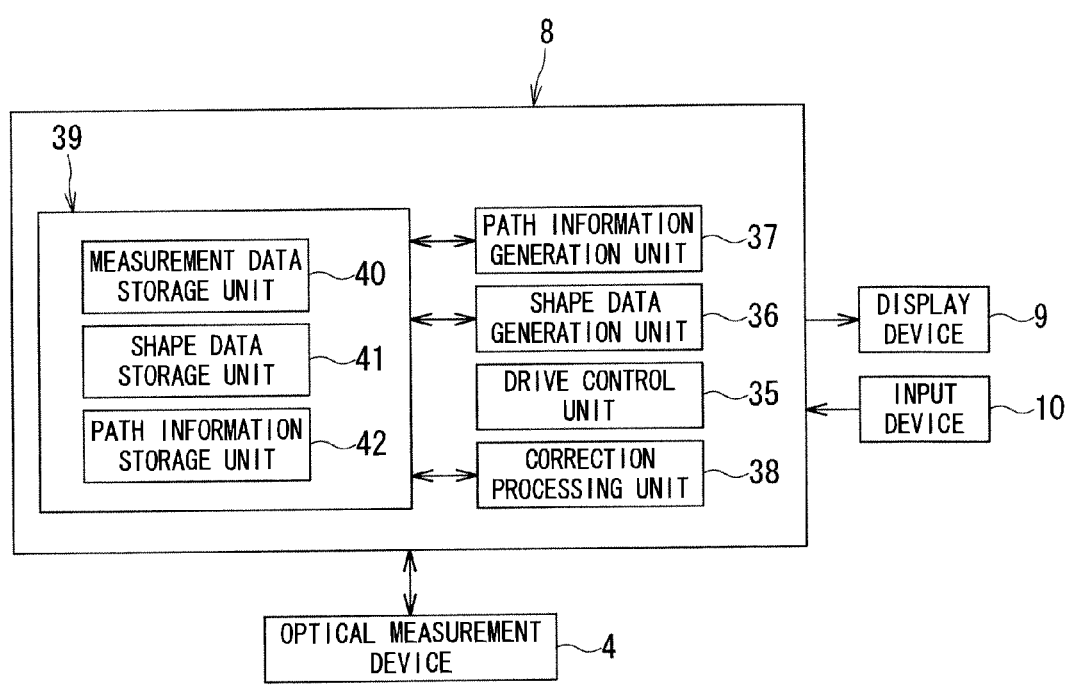
FIG. 4 is a functional configuration diagram illustrating the optical measurement device and a path information generation device provided in an apparatus body.

FIG. 4 is a functional configuration diagram illustrating the optical measurement device 4, and the path information generation device 8 in the apparatus body 5.

The optical measurement device 4 applies the laser light L onto the two-dimensional surface in accordance with an instruction input from the input device 10 to a drive control unit 35 in the path information generation device 8. The optical measurement device 4 also measures a distance to an application point on the surface of the object to be inspected 21 placed on the scanning stage 3a in a non-contact state and obtains measurement data. In order to generate scanning path information with high accuracy in a generation process of the scanning path information performed thereafter, it is desirable that the measurement data including a group of multiple points at minute intervals is obtained on the surface of the object to be inspected 21. Measurement data at M points is obtained in the X-axis direction, measurement data at N points is obtained in the Y-axis direction, and the points are set as (Pi, j) (i=1, 2, ..., M, j=1, 2, ..., N). The measurement data at each point (Pi, j) obtained from the optical measurement device 4 is transmitted to the path information generation device 8 and stored in a measurement data storage unit 40.

As shown in FIG. 4, the path information generation device 8 in the apparatus body 5 includes a shape data generation unit 36, a path information generation unit 37, the drive control unit 35, a correction processing unit 38 and a storage unit 39. The storage unit 39 includes a measurement data storage unit 40, a shape data storage unit 41, and a path information storage unit 42. The correction processing unit 38 will be described later in detail.

The shape data generation unit 36 reads the measurement data (Pi, j) including the group of points transmitted from the optical measurement device 4 and stored in the measurement data storage unit 40 and then generates the shape data of the surface of the object to be inspected 21.

Figure 5:
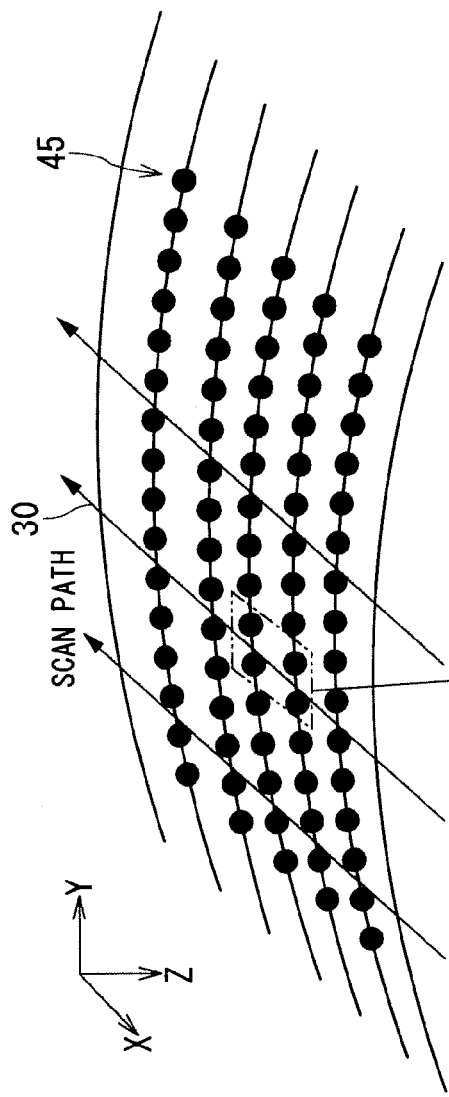
FIG. 5(A) shows a group of points of shape data.
FIG. 5(B) is an enlarged view of a portion of the group of points of the shape data.
Figure 5:
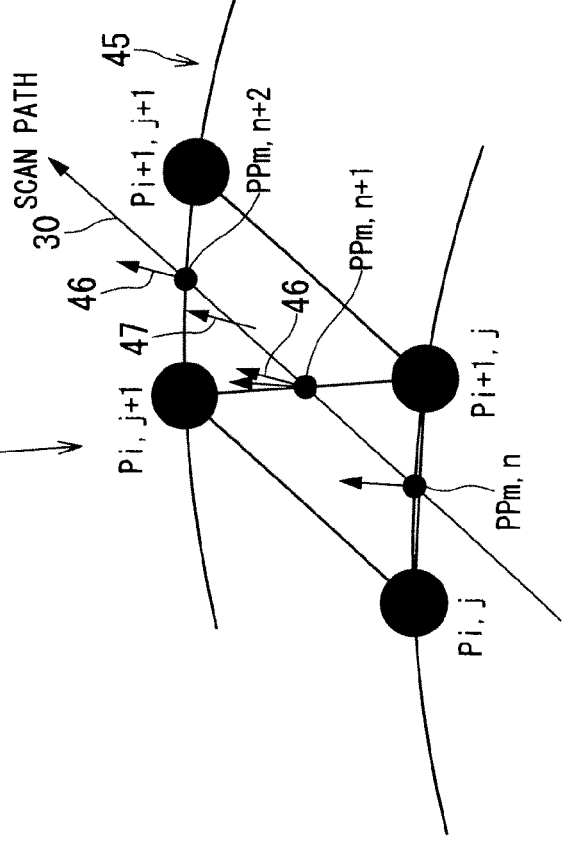

FIG. 5(A) shows a group of points of shape data 45.

Generation of the shape data 45 by the shape data generation unit 36 is achieved by converting measurement data on a distance between the optical measurement device 4 and the application point on the surface of the object to be inspected 21 into a coordinate system of the scanner mechanism 3, that is, a coordinate value (X, Y, Z) of an X-axis, a Y-axis and a Z-axis that intersect each other. Position information of the group of points of the shape data 45 on the surface of the object to be inspected 21 represented by the coordinate system of the scanner mechanism 3 is stored in the shape data storage unit 41.

The path information generation unit 37 reads the shape data 45 generated by the shape data generation unit 36 and stored in the shape data storage unit 41, and then, generates scanning path information for driving the scanner mechanism 3 on the object to be inspected 21. The scanning path information is information on the scanning path formed by a combination of movements of scanning a required length in the X-axis direction perpendicular to an opening width of the ultrasonic transducer, then shifting in the Y-axis direction by the opening width of the ultrasonic transducer, and scanning a required length in the opposite X-axis direction.

The scanning path information is generated so as to pass on or between the points of the shape data 45 shown in FIG. 5(A). When the scanning path 30 passes on the points, coordinate values (X, Y, Z) provided to these points are passage points on the scanning path.

Meanwhile, when the scanning path 30 passes between the points, an interpolation is performed between points adjacent to the scanning path 30 in the group of points of the shape data 45, and the coordinate values (X, Y, Z) as position information of passage points required for generating scanning path information are obtained as passage points on the scanning path.

FIG. 5(B) is an enlarged view of a part of the group of points of the shape data 45 in FIG. 5(A).

Specifically, the coordinate values (X, Y, Z) of points ((PPm, n+1), (PPm, n+2)) at which sides of a triangle formed by a group of three points (for example, (Pi, j+1), (Pi+1, j), (P1+1, j+1)) adjacent to the scanning path 30 intersect the scanning path 30 are calculated by a linear interpolation between the points. A coordinate value (X, Y, Z) of a different passage point (PPm, n) is similarly calculated by a linear interpolation between three points ((Pi, j), (Pi, j+1), (Pi+1, j)) forming a triangle. The path information generation unit 37 performs such a linear interpolation for each passage point where the scanning path intersects the sides of the triangle formed by the group of three points, and connects obtained passage points in order of the scanning path, thereby obtaining scanning path information.

The interpolation of the passage points may be performed between two points or three or more points without being limited to the three points.

A normal vector 46 of each passage point that forms the scanning path 30 is calculated so that the ultrasound emitted from the ultrasonic transducer 2 is substantially perpendicularly incident on the surface of the object to be inspected 21, and a constant distance is always maintained between the surface of the object to be inspected 21 and the center of the opening surface of the ultrasonic transducer 2. As the normal vector 46 of each passage point that forms the scanning path 30, a normal vector 47 of a triangle formed by the group of three points is calculated, and the normal vector 47 is regarded as a normal vector 46 of a point at which a side of the triangle intersects the scanning path 30, that is, each passage point forming the scanning path, and this normal vector is applied. The group of points of the measurement data are obtained at minute intervals, thereby avoiding occurrence of a large deviation even if the normal vector 47 of the triangle is regarded as the normal vector 46 of each passage point.

The path information generation unit 37 uses the normal vector 46 of each passage point thus calculated to calculate a rotation amount of the A-axis rotating portion 3e so that the normal vector 46 of each passage point on the scanning path 30 always intersects the opening surface of the ultrasonic transducer 2. Position information of the passage point is determined so as to make always constant a distance between the center of the opening surface of the ultrasonic transducer 2 and each passage point.

Thus, the scanning path information can be generated so that the ultrasound emitted from the ultrasonic transducer 2 can be perpendicularly incident on the surface of the object to be inspected 21, and accordingly, the distance between the center of the opening surface of the ultrasonic transducer 2 and the surface of the object to be inspected 21 is always made to be constant.

The scanning path information thus generated is provided by the coordinate value (X, Y, Z) in the coordinate system of the scanner mechanism 3 and the rotation amount of the A-axis rotating portion 3e and is then stored in the path information storage unit 42 in the path information generation device 8. The scanner mechanism driving device 7 in the apparatus body 5 reads the scanning path information stored in the path information storage unit 42 and controls the scanner mechanism 3.

Figure 6:
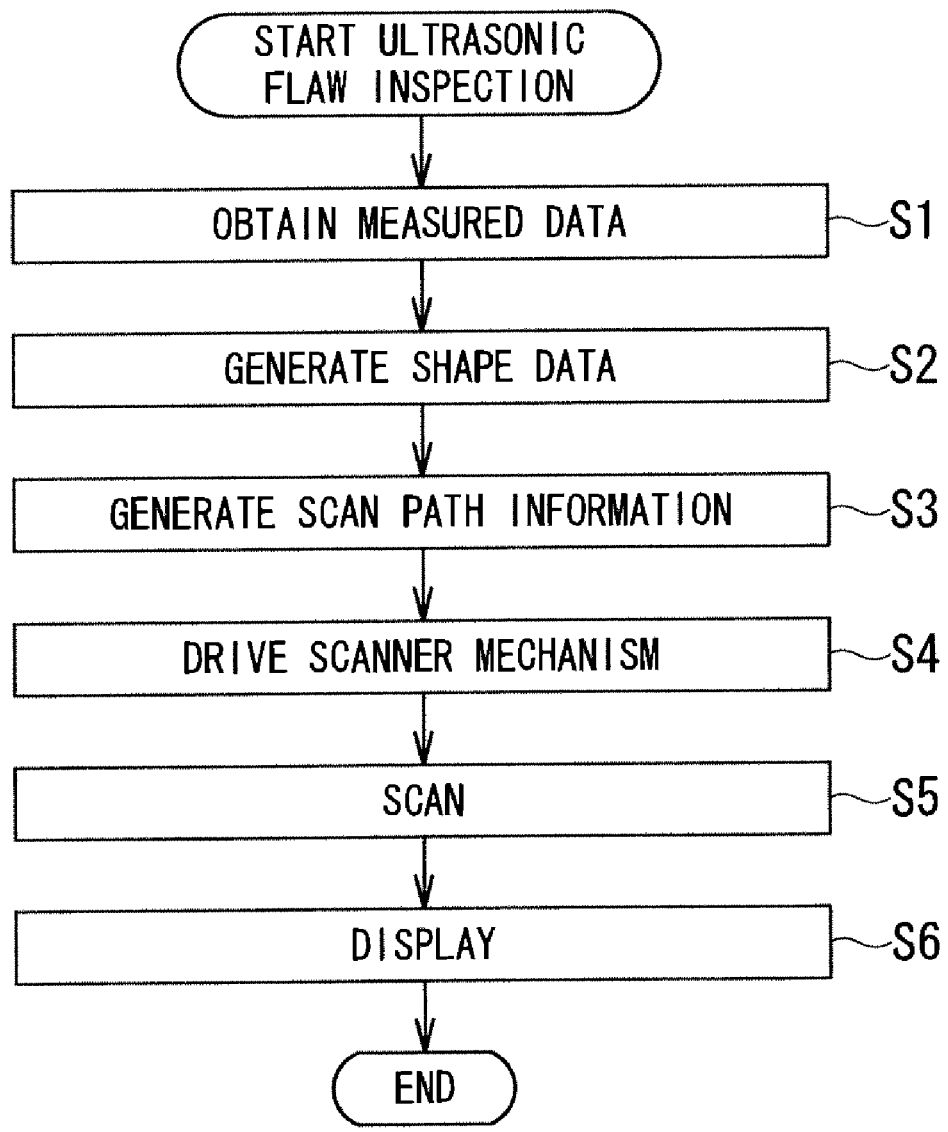
FIG. 6 is a flowchart illustrating an ultrasonic flaw inspection using the ultrasonic inspection apparatus of the embodiment.

Next, the ultrasonic flaw inspection using the ultrasonic inspection apparatus 1 of this embodiment will be described hereunder with reference to FIG. 6.

In the ultrasonic flaw inspection using the ultrasonic inspection apparatus 1, the object to be inspected 21 is placed on the scanning stage 3a of the scanner mechanism 3, and the ultrasonic flaw inspection is started on the basis of an instruction input by the input device 10 to thereby start the inspection.

In step S1, the optical measurement device 4 applies a laser light L to the object to be inspected 21 placed on the scanning stage 3a. The optical measurement device 4 obtains a group of points, whose distances to the application point on the surface of the object to be inspected 21 are measured without contact, and stores the group of points as measurement data in the measurement data storage unit 40. The group of points of the measurement data are desirably obtained at minute intervals to generate scanning path information with high accuracy.

In step S2, the shape data generation unit 36 reads the measurement data obtained in the measurement data obtaining step S1 and stored in the measurement data storage unit 40, and generates shape data 45 having position information converted into a coordinate value (X, Y, Z) in the coordinate system of the scanner mechanism 3 on the surface of the object to be inspected 21. The generated shape data 45 is stored in the shape data storage unit 41.

In step S3, the path information generation unit 37 in the path information generation device 8 reads the shape data stored in the shape data storage unit 41 in the shape data generation step S2, and generates scanning path information for the ultrasonic transducer 2 to scan the object to be inspected 21. The generated scanning path information is stored in the path information storage unit 42 in the storage unit 39. The scanning path information is generated by performing an interpolation operation by using the group of points of the shape data 45, calculating the position information and a normal vector 46 of a passage point, then calculating the coordinate (X, Y, Z) of the passage point and the rotation amount of the A-axis rotating portion 3e so that the normal vector 46 of each passage point intersects the opening surface of the ultrasonic transducer 2, and the distance between the center of the opening surface of the ultrasonic transducer 2 and the surface of the object to be inspected 21 is always constant, and connecting the coordinates and the rotation amounts in order of the scanning path.

In step S4, the scanner mechanism driving device 7 reads the scanning path information 30 stored in the path information storage unit 42 in the path information generation step S3 based on an input from the input device 10 or the like. The driving device 7 drives the X-axis driving portion 3c, the YZ-axis driving portion 3d, and the A-axis rotating portion 3e of the scanner mechanism 3 based on the scanning path information 30.

In step S5, the ultrasonic transducer 2 scans the surface of the object to be inspected 21 according to the driving of the X-axis driving portion 3c, the YZ-axis driving portion 3d, and the A-axis rotating portion 3e of the scanner mechanism 3. The ultrasonic transducer 2 moves on and scans the surface of the object to be inspected 21 under the control of the flaw inspection device 6 in the apparatus body 5.

In step S6, a two- or three-dimensional flaw inspection image of the object to be inspected 21 obtained by scanning in the scanning step S5 is displayed on the display device 9. The ultrasonic flaw inspection is thus finished.

With the ultrasonic inspection apparatus 1, the optical measurement device 4 can be used to generate the group of points at minute intervals on the surface of the object to be inspected 21 as the shape data 45 with the object to be inspected 21 being placed on the scanning stage 3a of the scanner mechanism 3 for an actual ultrasonic flaw inspection. From the shape data 45 thus obtained, the scanning path information with extremely high accuracy can be generated without inclusion of a deviation in production or a deviation in placement of the object to be inspected 21 as in a conventional technology.

Even when the shape data 45 obtained using the optical measurement device 4 does not exist on the scanning path 30 of the ultrasonic transducer 2, the interpolation between the points at minute intervals of the shape data 45 adjacent to the scanning path is performed in an easy manner, thereby allowing a coordinate value on the scanning path 30 to be calculated without generation of a large deviation. This allows the scanning path information with high accuracy to be generated.

Further, based on the scanning path information with high accuracy, the ultrasound emitted from the ultrasonic transducer 2 can be perpendicularly incident on the surface of the object to be inspected 21, and a constant distance can be maintained between the center of the opening surface of the ultrasonic transducer 2 and the surface of the object to be inspected 21. This allows an ultrasonic flaw inspection to be performed with higher accuracy.

Further, the measurement data is obtained using the optical measurement device 4 such as a laser on the two-dimensional surface, and thus, it does not take an enormous time to obtain the measurement data on the surface of the object to be inspected 21 as required in the conventional technology, thereby performing the ultrasonic flaw inspection with high efficiency.

Specifically, the ultrasonic inspection apparatus 1 of this embodiment can drive the scanner mechanism 3 with high accuracy based on the scanning path information with high accuracy, and the performance of a two- or three-dimensional flaw inspection image of a defect 26 or the like by the ultrasonic flaw inspection can be improved with high efficiency.

Next, there will be described a case in which the scanning path information generated based on the measurement data obtained from the optical measurement device 4 is used as correction data, a correction process of scanning path information previously generated by a different method is performed, and the scanning path information with high accuracy used for the ultrasonic flaw inspection is generated.

A different method of previously generating the scanning path information includes the method of generating scanning path information by teaching and registering each passage point on a scanning path while actually driving the scanner mechanism on an object to be inspected. Alternatively, another different method includes a method of generating the scanning path information using computer software based on shape design data of an object to be inspected.

Furthermore, it is necessary for the scanning path information to generate the ultrasound so as to be perpendicularly incident on the surface of the object to be inspected 21, and it is also necessary for the distance between the center of the opening surface of the ultrasonic transducer 2 and the surface of the object to be inspected 21 to be constant. However, it is difficult to achieve the scanning with high accuracy even using the scanning path information generated by either of the above-described methods.

Then, a correction process of the scanning path information obtained by such methods as mentioned above is performed using the ultrasonic inspection apparatus 1 of this embodiment, thereby increasing accuracy of the scanning path information, which is insufficient in the above methods.

The correction processing unit 38 in the scanning path generation device 8 uses, as correction data, the scanning path information generated for a part of the object to be inspected 21 using the optical measurement device 4, and performs a correction process of the different scanning path information previously generated.

In the correction process of this embodiment, as an example of a part of the object to be inspected 21, the scanning path information around each of opposing ends of the object to be inspected 21 is calculated. As an example of the different scanning path information previously generated, the scanning path information generated by computer software based on the shape design data of the object to be inspected is applied.

Figure 7:
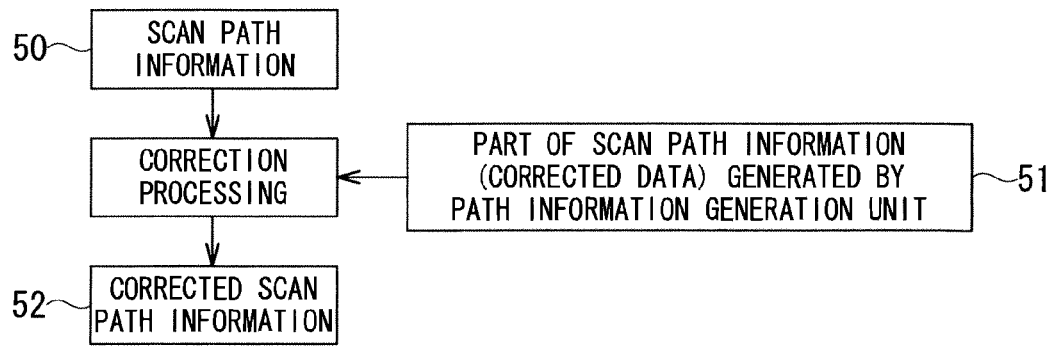
FIG. 7 illustrates a flow of data in a correction process.

FIG. 7 illustrates a flow of data in the correction process.

The optical measurement device 4 and the path information generation device 8 perform, as in the ultrasonic flaw inspection described with reference to FIG. 6, the processes in the measurement data obtaining step S1 to the scanning path information generation step S3 for a part of the object to be inspected 21 placed on the scanning stage 3a, and generates scanning path information 51 (hereinafter referred to as correction data 51) as correction data. The correction data 51 is transmitted to the correction processing unit 38, and the correction processing unit 38 receives the correction data 51.

Meanwhile, the correction processing unit 38 receives the scanning path information 50 (hereinafter referred to as scanning path information 50) previously generated by a different method and input from the input device 10 or the like.

Figure 8:
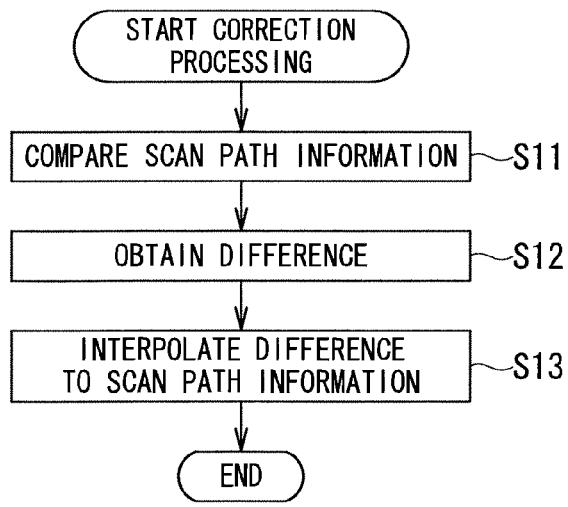
FIG. 8 is a flowchart illustrating a correction process of scanning path information.

FIG. 8 is a flowchart representing a correction process of the scanning path information performed in the correction processing unit 38 that receives the correction data 51 and the scanning path information 50.

In step S11, the correction processing unit 38 compares the correction data 51 with the scanning path information in the scanning path information 50 corresponding to the correction data 51. Specifically, the correction processing unit 38 compares the scanning path information around the opposing ends of the object to be inspected.

In step S12, the correction processing unit 38 calculates a difference between the correction data 51 and the scanning path information 50 based on the comparison performed in the comparison step S11.

In step S13, the correction processing unit 38 performs an interpolation of the scanning path of the entire scanning path information 50 based on the difference obtained in the difference obtaining step S12, and generates corrected scanning path information. The corrected scanning path information is stored in the path information storage unit 42 in the path information generation device 8, and the correction process is then finished.

With the ultrasonic inspection apparatus 1, even for the scanning path information previously generated by a different method, the correction data based on the scanning path information matching an actual ultrasonic flaw inspection can be generated. Thus, even for the scanning path information with which the scanning of the object to be inspected with high accuracy cannot be achieved, the correction process is performed with the correction data, thus performing the correction of the scanning path information with high accuracy.

For the scanning path information previously generated based on the shape design data or the like, it is supposed that a shape of the actual object to be inspected does not match a shape of the object to be inspected on the shape design data due to working accuracy at the time of production. However, the correction process is performed to generate the scanning path information with high accuracy without including a production deviation or a placement deviation which may be generated during the production.

Specifically, the ultrasonic inspection apparatus 1 of this embodiment can drive the scanner mechanism 3 with high accuracy based on the scanning path information with high accuracy corrected by the correction process. The ultrasonic inspection apparatus 1 can increase accuracy of the two- or three-dimensional flaw inspection image of the defect 26 or the like by the ultrasonic flaw inspection.

Next, a correction data obtaining process for correcting shape design data used for generating scanning path information required for the ultrasonic flaw inspection will be described.

As described above, conventionally, the scanning path information is generated by a method of generating the scanning path information using computer software based on the shape design data in a production process of an object to be inspected.

When the scanning path information is generated based on the shape design data, it is supposed that a shape of an actual object to be inspected does not match a shape of an object to be inspected on the shape design data due to working accuracy in the production process. With the scanning path information generated using the shape design data with such a mismatch, an ultrasonic flaw inspection is not achieved with high accuracy.

Thus, the ultrasonic inspection apparatus 1 of this embodiment is used to generate precise shape data of the object to be inspected. The generated shape data is used to correct shape design data, and generate the scanning path information based on the corrected shape design data. Thus, the scanning path information can be generated with high accuracy by using a conventional method of generating scanning path information using computer software.

Figure 9:
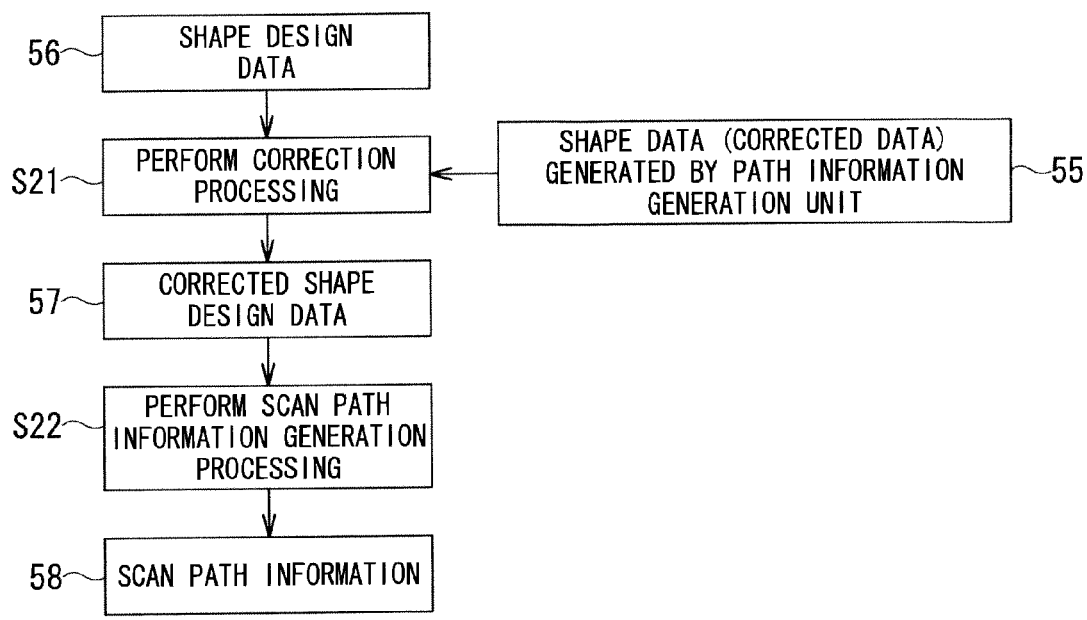
FIG. 9 is a flowchart illustrating a flow of data in a correction process of shape design data.

FIG. 9 is a flowchart illustrating a flow of data in a correction process of shape design data.

As in the ultrasonic flaw inspection described with reference to FIG. 6, the processes from the measurement data obtaining step S1 to the shape data generation step S2 are performed for the object to be inspected 21 placed on the scanning stage 3a, and shape data 55 (hereinafter referred to as correction data 55) of the obtained group of points is generated.

The generated correction data 55 and shape design data 56 of the object to be inspected 21 that receives an input from the input device 10 or the like are transmitted to the correction processing unit 38. The correction processing unit 38 receives the correction data 55 and the shape design data 56 of the object to be inspected 21.

The correction processing unit 38 receiving the correction data 55 and the shape design data 56 of the object to be inspected 21 performs the correction process of the shape design data 56. The correction processing unit 38 performs an interpolation of the entire shape data of the object to be inspected 21 based on the difference between the shape data of the correction data 55 and the shape design data, and generates corrected shape design data 57 (step S21).

The generated and corrected shape design data 57 is stored in the shape data storage unit 40 and then output to the display device 9 including the display unit, the calculation unit, the storage unit, and the like, and scanning path information 58 is generated using computer software (step S22). The correction process of the shape design data 56 is thus finished.

With the ultrasonic inspection apparatus 1, the correction process of the shape design data 56 in which the shape of the actual object to be inspected does not match the shape of the object to be inspected on the shape design data due to working accuracy in the production process is performed using the shape data 55 with high accuracy, and thus, the shape design data 57 with no production deviation or placement deviation can be generated, thereby generating the scanning path information 58 with high accuracy.

Furthermore, the ultrasonic inspection apparatus 1 is also advantageous in that the shape data generated using the optical measurement device 4 and the path information generation device 8 can be used as correction data to correct the existing scanning path information or shape data.

Specifically, the ultrasonic inspection apparatus 1 of this embodiment can drive the scanner mechanism 3 with high accuracy based on the scanning path information with high accuracy generated by performing the correction process, and can increase accuracy of a two- or three-dimensional flaw inspection image of the defect 26 or the like by the ultrasonic flaw inspection.

It is to be noted that although the optical measurement device 4 obtains measurement data of a three-dimensional shape of the object to be inspected 21 measured using the laser light L as an example of an optical way, the present invention is not limited to this embodiment, and a different optical way such as a CCD (charge-coupled device) or a fringe shape of moiré fringes may be used to obtain measurement data.

As an example of the object to be inspected, although the application of the object 21 having a cylindrical surface is described, the present invention is not limited to this example, and the object to be inspected 21 may have other shapes such as spherical or flat shape.

Furthermore, as the rotating portion of the scanner mechanism 3, although only the A-axis rotating portion 3e around the A-axis that is the rotation axis in the X-axis direction is provided, the rotation axes in the Y-axis and Z-axis directions may be provided.

Still furthermore, when the scanning path information is generated based on the shape data 45, the shape data at the three adjacent points is used to calculate the passage point, but not limited to example, and for example, the passage point and the scanning path information may be generated using shape data at four points.

The invention claimed is:

1. An ultrasonic inspection apparatus comprising:
an ultrasonic transducer including a plurality of piezoelectric transducers;
a flaw inspection device including a driving element selection unit connected to the plurality of piezoelectric transducers and adapted to select a required piezoelectric transducer in response to a drive signal from a signal generation unit, a signal detection circuit that causes ultrasound emitted from the piezoelectric transducer selected by the driving element selection unit to be incident on an object to be inspected, receives a reflection echo of the ultrasound, and detects an electric signal of the reflection echo, and a signal processing unit that calculates the detected electric signal of the reflection echo to thereby generate image information of an inside of the object to be inspected;
a scanner mechanism including a driving section that moves the ultrasonic transducer in three axial directions intersecting each other on the object to be inspected, and a rotating section that rotates the ultrasonic transducer around a rotation axis in at least one axial direction among the three axial directions;
a measurement unit measuring a distance to a surface of the object to be inspected to obtain measurement data including a group of points;

a shape data generation unit, by using the measurement data including the group of points obtained by the measurement unit, for generating shape data of the surface of the object to be inspected including the group of points having position information represented by a coordinate system of the scanner mechanism; and a path information generation unit, by using the shape data generated by the shape data generation unit, for calculating a passage point on the surface of the object to be inspected that forms a scanning path of the ultrasonic transducer, and generating the scanning path information of the ultrasonic transducer in which a normal vector of the passage point on the surface of the object to be inspected and an opening surface of the ultrasonic transducer intersect each other, and a distance between the passage point and a center of the opening surface of the ultrasonic transducer is constant, wherein when a passage point on the surface of the object to be inspected is not included in a group of points that constitute the shape data, the path information generation unit performs an interpolation using the group of points that constitute the shape data so as to calculate the passage point, and the path information generation unit performs an interpolation using at least two points that are adjacent to the scanning path of the ultrasonic transducer and constitute the shape data so as to calculate a passage point on the surface of the object to be inspected.

2. The ultrasonic inspection apparatus according to claim 1, wherein the path information generation unit calculates a normal vector of a triangle formed by three points that are adjacent to a passage point on the surface of the object to be inspected and constitute the shape data, and generates the scanning path information using the normal vector of the triangle as the normal vector of the passage point.

3. The ultrasonic inspection apparatus according to claim 1 or 2, wherein the scanner mechanism further includes a scanning stage on which the object to be inspected is placed, and the driving section is operated to move the ultrasonic transducer in three axial directions that intersect each other on the scanning stage.

4. The ultrasonic inspection apparatus according to claim 1, further comprising a correction processing unit that sets at least a part of the scanning path information generated by the path information generation unit as correction data, obtains a difference between the correction data and different scanning path information previously generated, and performs a correction process of the different scanning path information previously generated based on the difference.

5. The ultrasonic inspection apparatus according to claim 1, further comprising a correction processing unit that sets the shape data generated by the shape data generation unit as correction data, obtains a difference between the correction data and shape design data of the object to be inspected, and performs a correction process of the shape design data based on the difference.

* * * * *